(12) United States Patent
De'Ath et al.

(10) Patent No.: US 6,639,097 B1
(45) Date of Patent: Oct. 28, 2003

(54) FUNGICIDES

(75) Inventors: Norman John De'Ath, Cambridge (GB); John Klostermyer, Bernardsville, NJ (US)

(73) Assignee: Bayer Cropscience GmbH (DE)

( * ) Notice: Subject to any disclaimer, the term of this patent is extended or adjusted under 35 U.S.C. 154(b) by 0 days.

(21) Appl. No.: 10/088,379

(22) PCT Filed: Sep. 15, 2000

(86) PCT No.: PCT/EP00/09360

§ 371 (c)(1),
(2), (4) Date: Jul. 29, 2002

(87) PCT Pub. No.: WO01/21626

PCT Pub. Date: Mar. 29, 2001

(30) Foreign Application Priority Data

Sep. 17, 1999 (GB) .............................. 9921930

(51) Int. Cl.$^7$ ............................................ C07C 271/06
(52) U.S. Cl. ..................................................... 560/169
(58) Field of Search ........................ 423/316; 564/463; 560/129, 159, 169

(56) References Cited

U.S. PATENT DOCUMENTS 6,339,103 B1 * 1/2002 De'Ath et al. .............. 514/478
6,358,938 B1 * 3/2002 Donnadieu et al. ......... 514/141

FOREIGN PATENT DOCUMENTS

| WO | 98/44801 | 10/1998 |
|----|----------|---------|
| WO | 99/42468 | 8/1999 |

OTHER PUBLICATIONS

H.B. Couch, et al., "Synergistic and Antagonistic Interactions of Fungicides Against Pythium Aphanidermatum on Perennial Ryegrass", *Crop Protection*, GB Elsevier Science, vol. 10, No. 5, Oct. 1, 1991, pp. 386–390.

* cited by examiner

*Primary Examiner*—Jean F. Vollano
(74) *Attorney, Agent, or Firm*—Ostrolenk, Faber, Gerb & Soffen, LLP

(57) ABSTRACT

This invention relates to a new fungicidally active compound of formula (I), a method of combating fungi at a locus infested or liable to be infested therewith, and an agricultural composition where X is H or $O^-A^+$ and A is a radical (II).

1 Claim, No Drawings

FUNGICIDES

This is a 371 of PCT/EP00/09360 filed Sep. 15, 2000, now WO01/21626.

This invention relates to a new compound having fungicidal activity.

In one aspect, the invention provides a compound of formula I

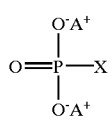
(I)

where X is hydrogen or O$^-$A$^+$ and A is a radical

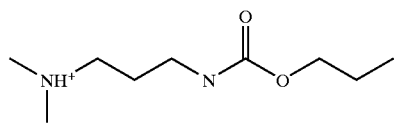

The two compounds resulting are dimethyl-[3-(propoxycarbonylamino)propyl]-ammonium phosphate and dimethyl-[3-(propoxycarbonylamino)propyl]ammonium phosphite.

The compounds of the invention have activity as fungicides, especially against Phycomycete diseases of plants. e.g. vine downy mildew (*Plasmopara viticola*), various Phytophthora blights e.g. late tomato or potato blight (*Phytophthora infestans*), Pythium spp., Aphanomyces spp., Bremia spp., Perenospora spp. and Pseudoperenospora spp.

The invention thus also provides a method of combating fungi at a locus infested or liable to be infested therewith, which comprises applying to the locus the compounds of the invention.

The invention also provides an agricultural composition comprising the compounds of the invention in admixture with an agriculturally acceptable diluent or carrier.

The composition can comprise one or more additional active ingredients, for example compounds known to possess plant-growth regulant, herbicidal, fungicidal, insecticidal or acaricidal properties. Alternatively the compound of the invention can be used in sequence with the other active ingredient.

Fungicides with which the compound can be mixed include acylanilines, such as metalaxyl, oxadixyl, ofurace, benalaxyl and furalaxyl; cymoxanil; mancozeb; chlorothalonil; folpet; captan; famoxadone; fenamidone; spiroxamine; fluazinam; dimethomorph; strobilurins, such as kresoxim-methyl, azoxystrobin and trifloxystrobin, pyrimethanil, cyprodinil; mepanipyrim; and iprodione.

The names quoted for these compounds are the non-proprietary common names and the chemical structure can be found for example by reference to the "Pesticide Manual", eleventh edition, 1997, published by the British Crop Protection Council. Of the compounds whose common names are not mentioned in the Pesticide Manual the full chemical names are as follows:

trifloxystrobin—methyl (E,E)-methoxyimino-{2-[1-(3-trifluoromethylphenyl)-ethylideneaminooxymethyl]phenyl}acetate spiroxamine—8-tert-butyl-1,4-dioxaspiro[4. 5]decan-2-ylmethyl(ethyl)-(propyl)amine fenamidone—(S)-1-anilino-4-methyl-2-methylthio-4-phenylimidazolin-5-one The composition of the invention may include for example a dispersing agent, emulsifying agent or wetting agent. Usually they are in the form of an aqueous concentrate.

The concentration of the active ingredient in the composition of the present invention, as applied to plants is preferably within the range of 0.0001 to 1.0 per cent by weight, especially 0.0001 to 0.01 per cent by weight. In a primary composition, the amount of active ingredient can vary widely and can be, for example, from 5 to 95 per cent by weight of the composition.

In the method of the invention the compound is generally applied to seeds, plants or their habitat. Thus, the compound can be applied directly to the soil before, at or after drilling so that the presence of active compound in the soil can control the growth of fungi which may attack seeds. When the soil is treated directly the active compound can be applied in any manner which allows it to be intimately mixed with the soil such as by spraying, by broadcasting a solid form of granules, or by applying the active ingredient at the same time as drilling by inserting it in the same drill as the seeds. A suitable application rate is within the range of from 5 to 1000 g per hectare, more preferably from 10 to 500 g per hectare.

Alternatively the active compound can be applied directly to the plant by, for example, spraying or dusting either at the time when the fungus has begun to appear on the plant or before the appearance of fungus as a protective measure. In both such cases the preferred mode of application is by foliar spraying. It is generally important to obtain good control of fungi in the early stages of plant growth as this is the time when the plant can be most severely damaged. The spray or dust can conveniently contain a pre- or post-emergence herbicide if this is thought necessary. Sometimes, it is practicable to treat the roots of a plant before or during planting, for example, by dipping the roots in a suitable liquid or solid composition. When the active compound is applied directly to the plant a suitable rate of application is from 0.025 to 5 kg per hectare, preferably from 0.05 to 1 kg per hectare.

The compounds of formula I may be obtained by reacting an amine of formula II

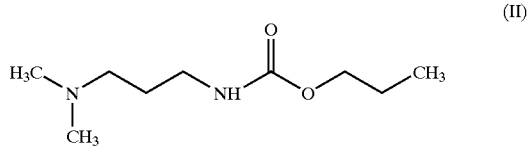
(II)

with phosphoric or phosphorous acid. In general it is desirable to react an acid addition of salt of the compound of formula II, e.g. the hydrochloride, with a salt of the phosphorus acid, e.g. an alkali metal salt, such as the sodium salt.

This reaction can be carried out in aqueous solution

The invention is illustrated in the following Example.

EXAMPLE 1

A solution of sodium phosphate dodecahydrate (8.8 g in water (75 ml)) was added to an aqueous solution of propyl-3-(dimethylamino)propylcarbamate hydrochloride (20 ml of concentration 776.9 g/l) in a further 75 ml of water. The mixture was stirred for 30 min, evaporated to dryness, dissolved in dichloromethane (200 ml) and the insoluble white solid (sodium chloride) filtered off. The filtrate was evaporated to leave dimethyl-[3-(propoxycarbonylamino)propyl]ammonium phosphate, as a viscous colorless oil.

Nmr spectroscopy confirmed that the product was a salt by observation of the chemical shifts relative to propyl 3-(dimethylamino)propylcarbamate.

EXAMPLE 2

A solution of phosphorous acid (2.87 g in water (50 ml)) was stirred for 1 hour with a solution of sodium hydroxide (2.8 g in water (50 ml)). Propyl 3-(dimethyiamino) propylcarbamate hydrochloride (15.7 g) in water (50 ml) was added and the mixture stirred for 30 min, evaporated to dryness, dichloromethane (450 ml) added and re-evaporated. The residue was dissolved in dichloromethane (150 ml) allowed to stand for 1 hour and the insoluble white solid (sodium chloride) filtered off. The filtrate was evaporated to leave dimethyl-[3-(propoxycarbonylamino)propyl]ammonium phosphite, as a viscous colorless oil.

Nmr spectroscopy confirmed that the product was a salt by observation of the chemical shifts relative to propyl 3-(dimethylamino)propylcarbamate.

What is claimed is:

1. A compound of formula I

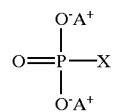

(I)

where X is hydrogen or O⁻A⁺ and A is a radical

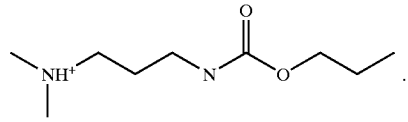

.

* * * * *